US008119398B2

(12) United States Patent
Sayre et al.

(10) Patent No.: US 8,119,398 B2
(45) Date of Patent: Feb. 21, 2012

(54) ADIPOSE-DERIVED STEM CELLS FOR TISSUE REGENERATION AND WOUND HEALING

(75) Inventors: Chauncey B. Sayre, Irvine, CA (US); Francisco J. Silva, Rancho Cucamonga, CA (US)

(73) Assignee: PrimeGen Biotech LLC, Irvine, CA (US)

( * ) Notice: Subject to any disclaimer, the term of this patent is extended or adjusted under 35 U.S.C. 154(b) by 965 days.

(21) Appl. No.: 11/323,276

(22) Filed: Dec. 30, 2005

(65) Prior Publication Data
US 2006/0147430 A1    Jul. 6, 2006

Related U.S. Application Data

(60) Provisional application No. 60/641,034, filed on Dec. 30, 2004.

(51) Int. Cl.
*C12N 15/00* (2006.01)
(52) U.S. Cl. ...................................... 435/325; 424/93.1
(58) Field of Classification Search ................. 424/93.1; 435/325
See application file for complete search history.

(56) References Cited

U.S. PATENT DOCUMENTS

| | | | |
|---|---|---|---|
| 4,298,002 | A | 11/1981 | Ronel et al. |
| 4,789,734 | A | 12/1988 | Pierschbacher |
| 4,792,525 | A | 12/1988 | Ruoslahti et al. |
| 4,879,237 | A | 11/1989 | Rudslahti et al. |
| 4,892,538 | A | 1/1990 | Aebischer et al. |
| 4,988,621 | A | 1/1991 | Ruoslahti et al. |
| 5,011,472 | A | 4/1991 | Aebischer et al. |
| 5,308,701 | A | 5/1994 | Cohen et al. |
| 5,965,997 | A | 10/1999 | Alwardi et al. |
| 6,777,231 | B1 | 8/2004 | Katz et al. |
| 2002/0076400 | A1 | 6/2002 | Katz et al. |
| 2003/0054331 | A1 | 3/2003 | Fraser et al. |
| 2003/0082152 | A1 | 5/2003 | Hedrick et al. |
| 2003/0161816 | A1 | 8/2003 | Fraser et al. |
| 2004/0096431 | A1 | 5/2004 | Fraser et al. |
| 2004/0171146 | A1 | 9/2004 | Katz et al. |

FOREIGN PATENT DOCUMENTS

| | | |
|---|---|---|
| WO | 91/10425 | 7/1991 |
| WO | 91/10470 | 7/1991 |
| WO | 00/53795 | 9/2000 |
| WO | 01/19966 | 3/2001 |
| WO | 03/022988 | 3/2003 |
| WO | 03/024215 | 3/2003 |
| WO | 03/053346 | 7/2003 |
| WO | 2004/074457 | 9/2004 |

OTHER PUBLICATIONS

Zuk (Mol. Biol. of the Cell, Dec. 2002, vol. 13, p. 4279-4295).*
De Almeida (J. Urology, Apr. 27, 2003, vol. 169, No. 4, Suppl., p. 35-36, Abstract 136).*
De Almeida (J. Urology, Apr. 27, 2003, vol. 169, No. 4, Suppl., p. 125, Abstract 482).*
De Almeida (J. Urology, Apr. 27, 2003, vol. 169, No. 4, Suppl., p. 102, Abstract 396).*
Ogawa (J. Nippon Med. School, Aug. 2004, vol. 71, No. 4, p. 240-241).*
Rodriguez (Biochem. Biophys. Res. Comm., Mar. 5, 2004, vol. 315, p. 255-263).*
Liu (Shiyong Kouqiang Yixue Zazhi, 2003, vol. 19, No. 6, p. 554-557).*
Zuk (Tissue Engineering, 2001, vol. 7, No. 2, p. 211-228).*
Mizuno (Plast. Reconstr. Surg, 2002, vol. 109, p. 199-209).*
Ogawa (Biochemical and Biophysical Res. Comm., 2004, vol. 313, p. 871-877).*
Cima, LG et al., Hepatocyte culture on biodegradable polymeric substrates. Biotechnol. Bioeng. 38:145-158, 2004.
Lacy, PE et al., Maintenance of normoglycemia in diabetic mice by subcutaneous xenografts of encapsulated islets. Science, 254:1782-4, 1991.
Sullivan, SJ et al., Biohybrid artifical pancreas: long-term implantation studies in diabetic, pancreatectomized dogs. Science, 252:718-21, 1991.
Vacanti, JP et al., Selective cell transplantation using bioabsorbable artificial polymers as matrices. J Pediatr Surg. 23:3-9, 1988.
Vacanti, CA et al., Synthetic polymers seeded with chondrocytes provide a template for new cartilage formation. Plast Reconstr Surg., 88:753-9, 1991.
Han, S-K et al., The effect of transplantation of human mesenchymal stem cells and dermal fibroblasts on the angiogenesis. Plastic Surgery 2003, San Diego, CA, Abstract 3235.
Zhou, S et al., The ABC transporter Bcrp1/ABCG2 is expressed in a wide variety of stem cells and is a molecular determinant of the side-population phenotype. Nature Medicine 7:1028-1034, 2001.
Hauner H et al. Adipose tissue development: the role of precursor cells and adipogenic factors. Part I: Adipose tissue development and the role of precursor cells. Klin Wochenschr 65(17):803-11, 1987.
Zuk PA et al. Human adipose tissue is a source of multipotent stem cells, Mol Biol Cell. 13(12):4279-95, 2002.
Zuk PA et al. Multilineage cells from human adipose tissue: implications for cell-based therapies. Tissue Eng. 7 (2):211-28, 2001.
Alvi AJ et al. Functional and molecular characterisation of mammary side population cells. Breast Cancer Res. 5((1): R1-8, 2003, Epub Oct. 14, 2002.

(Continued)

*Primary Examiner* — Michael C. Wilson
(74) *Attorney, Agent, or Firm* — K & L Gates LLP; Louis C. Cullman; Michelle Glasky Bergman

(57) ABSTRACT

Compositions and methods for promoting tissue regeneration, particularly skin regeneration, with adipose-derived stem cells are provided. Additionally methods and compositions for promoting tissue regeneration with adipose-derived stem cell side population cells are provided. The adipose-derived cells are administered in a tissue regenerating effect amount optionally with a bioactive agent. Additionally the adipose derived cells can be autologous or syngeneic.

5 Claims, 8 Drawing Sheets

(4 of 8 Drawing Sheet(s) Filed in Color)

OTHER PUBLICATIONS

Bhatt RI et al. Novel method for the isolation and characterisation of the putative prostatic stem cell. Cytometry A. 54(2):89-99, 2003.

Bhattacharya S et al. Direct identification and enrichment of retinal stem cells/progenitors by Hoechst dye efflux assay. Invest Opthamol Vis Sci 44(6):2764-73, 2003.

Shimano K et al. Hepatic oval cells have the side population phenotype defined by expression of ATP-binding cassette transporter ABCG2/BCRP1. Am J Pathol. 163(1):3-9, 2003.

Summer R et al. Side population cells and Bcrp1 expression in lung. Am J Physiol Lung Cell Mol Physiol. 285(1): L97-104, 2003. Epub Mar. 7, 2003.

De Rooij DG et al. Leydig cells: testicular side population harbors transplantable leydig stem cells. Endocrinology 145(9):4009-10, 2004.

Ogawa R et al. Chondrogenic and osteogenic differentiation of adipose-derived stem cells isolated from GFP transgenic mice. J Nippon Med Sch. 71(4):240-1, 2004.

Mizuno H et al. Myogenic differentiation by human processed lipoaspirate cells. Plast Reconstr Surg. 109 (1):199-209, 2002.

Peterson B et al. Healing of critically sized femoral defects using genetically modified mesenchymal stem cells from human adipose tissue. Tissue Eng. 11(1-2):120-9, 2005.

Seo MJ et al. Differentiation of human adipose stromal cells into hepatic lineage in vitro and in vivo. Biochem Biophys Res Comm. 328(1):258-64, 2005.

Hattori H et al. Osteogenic potential of human adipose tissue-derived stromal cells as an alternative stem cell source. Cell Tissues Organs. 178(1):2-12, 2004.

Safford KM et al. Stem cell therapy for neurologic disorders: therapeutic potential of adipose-derived stem cells. Curr Drug Targets. 6(1):57-62, 2005.

Guilak F et al. Adipose-derived adult stem cells for cartilage tissue engineering. Biorheology 42(3-4):389-99, 2004.

Orkin SH. Stem cell alchemy. Nat Med. 6(11):1212-3, 2000.

Bunting KD. ABC transporters as phenotypic markers and functional regulators of stem cells. Stem Cells 20 (1):11-20, 2002.

Orkin SH, Zon LI. Hematopoiesis and stem cells: plasticity versus developmental heterogeneity. Nat Immunol. 3 (4):323-8, 2002.

Cousin B et al. Reconstitution of lethally irradiated mice by cells isolated from adipose tissue. Biochem Biophys Res Comm. 301(4):1016-22, 2003.

Kim SJ et al. Human adipose stromal cells expanded in human serum promote engraftment of human peripehral blood hematopoietic stem cells in NOD/SCOD mice. Biochem Biophys Res Comm. 329:25-31, 2005.

Goodell MA. Introduction: Focus on hematology. CD34(+) or CD34(-): does it really matter? Blood 94(8):2545-7, 1999.

Ivanova NB et al. A stem cell molecular signature. Science 298(5593):601-4, 2002.

Morrison SJ et al. Identification of a lineage of multipotent progenitors. Development 124(10):1929-39, 1997.

Lassalle B et al. 'Side population' cells in adult mouse testis express Bcrp1 gene and are enriched in spermatogonia and germinal stem cells. Development 131(2):479-87, 2004. Epub Dec. 17, 2003.

Montanaro F et al. Demystifying SP cell purification: viability, yield and phenotype are defined by isolation parameters. Exp Cell Res. 298(1):144-54, 2004.

Fuchs E and Raghavan S, Getting under the skin of epidermal morphogenesis. Nature Reviews Genetics 3:199-209, 2002.

Pesce M and Scholer HR, Octo-4: Control of totipotency and germline determination. Mol Reprod Devel. 55:452-457, 2000.

Eaker S. et al. Detection and enrichment of hematopoietic stem cells by side population phenotype. Meth. In Molec. Biology. vol. 263:161-180, 2004.

Gussoni E. et al. Dystrophin expression in the MDX mouse restored by stem cell transplantation. Nature Publ. Group. vol. 401: 390-394, 1999.

Liu H.J. et al., Phenotypic and in vitro characterization of Hoechst 33342 side population in umbilical cord blood (abstract). Blood, W.B. Saunders Co.. vol. 96: 664a, 2000.

Josefsen D. et al. Hematopoietic side population (SP) cells are present in highly purified huma n CDd34+ cells from peripheral blood progenitor cells (PBPC)(abstract). Blood, W.B. Saunders Co.. vol. 98:124b, 2001.

\* cited by examiner

ADIPOSE-DERIVED STEM CELLS FOR TISSUE REGENERATION AND WOUND HEALING

CROSS-REFERENCE TO RELATED APPLICATIONS

The present application claims priority under 37 CFR §119 (e) to U.S. Provisional Patent Application No. 60/641,034 filed Dec. 30, 2004.

FIELD OF THE INVENTION

The present invention provides compositions, including adipose-derived stem cells and adipose-derived stem cell side population cells, for promoting tissue regeneration, particularly skin regeneration. Additionally, the present invention provides methods for inducing tissue regeneration and wound healing.

BACKGROUND OF THE INVENTION

Stem cells have been shown to repopulate and repair tissues, organs and/or organ systems. Of interest for regenerative medicine is the use of adult or post-natal stem cells for cell-based therapies. One particular type of post-natal stem cell is an adipose-derived stem cell which is found in the connective tissues within adipose tissue. Adipose-derived stem cells have exhibited multi-potency in vitro by being able to differentiate into cardiogenic, neurogenic, osteogenic, adipogenic and chondrogenic cell types after exposure to the appropriate differentiating environment. In vivo, adipose-derived stem cells have been demonstrated to successfully form new bone and near complete calvarial continuity around the area of skull trauma.

Adipose tissue derived from the mesenchyme contains a supportive stroma that is easily isolated. As a result, adipose tissue may represent a valuable source of stem cells. Adipose tissue derives from the mesoderm and is composed of two different cell populations, mature adipose cells and the stroma vascular fraction. This fraction contains several cell types among which are pre-adipocytes. The stroma vascular fraction cells appear to have multiple mesodermal lineage capabilities in vitro, differentiating toward osteogenic, chondrogenic, and myogenic lineages in addition to adipogenic.

An increasing number of studies have isolated stem cells from adipose tissue and have been successful in differentiating them into other cell types. Collectively, these studies provide evidence that adipose tissue contains an abundant, accessible, and replenishable source of adult stem cells that can be readily isolated.

It is estimated that eight million people per year in the United States suffer from wounds caused by mechanical trauma, vascular insufficiencies or diabetes and if these wounds are left untreated, death due to infection can occur. Occasionally these wounds never fully heal and the injury or trauma site may remain open for periods ranging from months to years. These wounds require long-term medical treatment, which in addition to the devastating health implications can become costly to the patient and/or the health care system.

An incision created by a surgeon, trauma as a result of blunt force or tissue death caused by a variety of diseases all undergo a similar process of wound healing. Wound healing occurs in three distinct phases. The inflammatory phase is characterized by inflammation at the site of the trauma. This phase is critical for healing and involves extensive cell migration. The second phase of wound healing is the proliferative phase, which is marked by epithelialization, angiogenesis, granulation tissue formation and collagen deposition. Angiogenesis, which involves new capillary formation, is used to deliver nutrients and maintain granulation. Without formation of new capillaries into the wound, required nutrients fail to reach the wound resulting in a chronically unhealed wound. The third and final stage of wound healing is the maturational phase wherein fibroblasts differentiate into collagen. The disposition of the connective tissue matrix and collagen undergoes a contraction, resulting in scar tissue. Although scar formation is critical to wound healing, excessive scar formation can have additional cosmetic and/or pathologic consequences, such as keloids and/or hypotrophic scars.

Scar formation occurs in all tissues and the adverse effects of scar formation include keloid, hypertrophic scars, burn contracture and scleroderma in skin; stricture, adhesions and chronic pancreatitis in the gastrointestinal tract; cirrhosis and biliary atresia in the liver; interstitial fibrosis and bronchopulmonary dysplasia in the lung; rheumatic disease and ventricular aneurysm in the heart; retrolental fibroplasia and diabetic retinopathy in the eye; transmission loss in nerves; ankylosis and osteoarthritis in the bones and glomerulonephritis in the kidney. The ability of a wound to heal with minimal scar formation can have a profound effect on the patient and on medical or surgical practice.

Therefore there exists a medical need for methods and compositions to promote wound healing by cellular regeneration therapy.

SUMMARY OF THE INVENTION

The present invention provides methods and compositions of adipose-derived stem cells (ADSC) and ADSC side population (ADSC-SP) cells for tissue regeneration, specifically wound healing, reduction of scar formation and skin regeneration.

In one embodiment of the present invention, a therapeutic composition is provided for promoting tissue regeneration in a mammal comprising isolated adipose-derived stem cells (ADSC). In another embodiment, the ADSC comprise ADSC side population (ADSC-SP) cells wherein the ADSC-SP cells comprise cell surface markers, including, but are not limited to, $Lin^-$, $Sca-1^+$, $CD90^+$, $CD34^{+/low}$, $CD13^{+/low}$, $CD117^-$ and $CD18^{+/low}$.

In an embodiment of the present invention, the therapeutic composition further comprises a pharmaceutically acceptable carrier.

In another embodiment, the therapeutic composition comprises a tissue regenerating effective amount of the ADSC and wherein the tissue regenerating effective amount of the ADSC is approximately 0.5 to approximately $5.0 \times 10^6$ cells/ 10 mm of treatment site per treatment site per day.

In yet another embodiment of the therapeutic composition of the present invention, the mammal is a human.

In one embodiment of the present invention, a method is provided for promoting tissue regeneration in a patient in need thereof comprising administering a tissue regenerating effective amount of ADSCs to a treatment site.

In another embodiment of the methods of the present invention, the ADSC comprise ADSC side population (ADSC-SP) cells wherein the ADSC-SP cells comprise cell surface markers including, but not limited to, $Lin^-$, $Sca-1^+$, $CD90^+$, $CD34^{+/low}$, $CD13^{+/low}$, $CD117^-$ and $CD18^{+/low}$.

In yet another embodiment of the methods of the present invention, the method comprises administering ADSC with an optional pharmaceutically acceptable carrier.

In another embodiment of the methods of the present invention, the method comprises administering a tissue regenerating effective amount of the ADSC and wherein the tissue regenerating effective amount of the ADSC is approximately 0.5 to approximately $5.0 \times 10^6$ cells/10 mm of treatment site per treatment site per day.

In yet another embodiment of the methods of the present invention, the ADSC are autologous or syngeneic.

In another embodiment of the methods of the present invention, the tissue regeneration is skin regeneration at the site of a wound and wherein the wound is caused by an event selected from the group consisting of disease, trauma, surgery, burns and bites.

In an embodiment of the methods of the present invention, the tissue regeneration includes, but is not limited to, cardiac muscle regeneration, neural tissue regeneration or vascular regeneration.

In yet another embodiment of the methods of the present invention, the tissue regeneration minimizes scarring at a wound site.

In one embodiment of the methods of the present invention, the administering step includes, but is not limited to, topical application, intradermal injection, intravenous injection and subcutaneous injection.

In another embodiment of the methods of the present invention, the method further comprises differentiating the ADSC into cells of the same tissue type as the tissue in need of regeneration.

In yet another embodiment of the methods of the present invention, the further comprises administering a biologically active agent and wherein the bioactive agent is a growth factor or an immunosuppressive agent. In another embodiment, the bioactive agent is administered by a route comprising systemic administration or local administration at the site of tissue regeneration.

In an embodiment of the methods of the present invention, the method further comprises the administration of hyperbaric oxygen therapy. In another embodiment, the method further comprises skin grafting.

In one embodiment of the present invention, an adipose derived stem cell side population (ADSC-SP) is provided comprising isolated mammalian ADSC-SP cells comprising the cell surface markers including, but not limited to, $Lin^-$, $Sca-1^+$, $CD90^+$, $CD34^{+/low}$, $CD13^{+/low}$, $CD117^-$ and $CD18^{+/low}$. In another embodiment, the mammal is a human.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
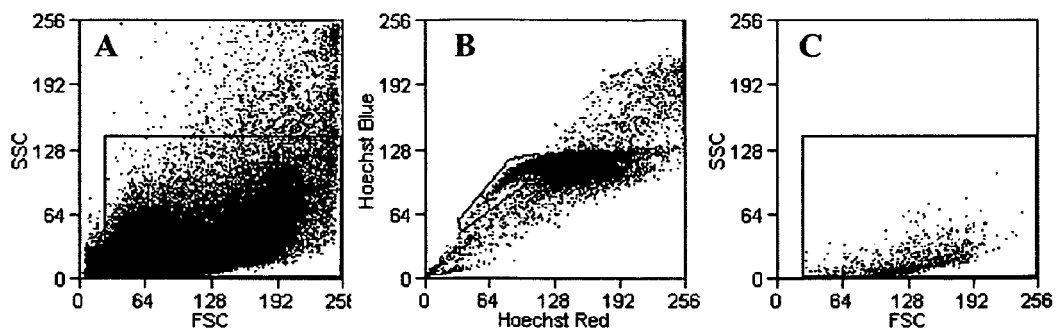
FIG. 1 depicts the flow cytometric identification of murine adipose-derived stem cell (ADSC) side population (SP) cells from freshly isolated adipose tissue according to the teachings of the present invention. (A) Forward and side scatter light profile of total adipocytes after tissue digestion; (B) Hoechst blue vs. Hoechst red emission of adipocytes gated from R1 (cells that expel Hoechst dye become dimmer and form the side population); (C) Backgate of R3 gated cells from Hoechst blue vs. Hoechst red to the original scatter plot.

The present invention provides adipose-derived stem cells (ADSC) and ADSC side population (ADSC-SP) cells from individuals for tissue regeneration, specifically wound healing, reduction of scar formation and skin regeneration in a mammal.

The term "mammal" as used herein, encompasses any mammal. Preferably a mammal is in need of such treatment or prevention. Examples of mammals include, but are not limited to, cows, horses, sheep, pigs, cats, dogs, mice, rats, rabbits, guinea pigs, monkeys, etc., more preferably, a human.

With the moral and ethical considerations of developing cell lines from human embryonic cells, the search for alternative sources of stem cells is underway. The alternative sources of adult stem cells have been found in many tissue types, including umbilical cord blood; mesenchymal tissue; skin; brain; bone marrow; adipose tissue and amniotic tissue.

Most stem cell preparations from whole tissue are a mixture of cells consisting of the stem cells and non-stem cells. More often than not, the non-stem cell population is much more abundant. Procedures to isolate stem cells are becoming much more prevalent and provide purified fractions of stem cells. Most isolation procedures include use of antibodies, nuclear dyes, or magnetic beads.

A possible candidate for a vast supply of adult stem cells is adipose tissue. Recent studies have shown that stem cells isolated from adipose tissue can differentiate and give rise to many cell types. This indicates that adult pluripotent stem cells exist in adipose tissue and have a high degree of plasticity.

A functional staining method using the DNA binding dye Hoechst 33342 has identified a rare population of cells from mouse bone marrow enriched for stem cells termed "side population" cells. Side population (SP) cells have additionally been identified in other tissue types.

The present inventors have identified the presence of SP cells in adult mouse adipose tissue, accounting for 1.0-1.5% of total adipocytes freshly isolated from mice 6-8 weeks of age. Side population cells were undifferentiated and quiescent ex vivo. In culture, adipose-derived SP cells proliferated at a slow rate on a layer of feeder cells providing leukemia inhibitory factor (LIF). In the culture system, adipose-derived SP cells attached to feeders, grew in colonies, and remained in an undifferentiated state. Leukemia inhibitory factor, important for the maintenance of embryonic stem cells in an undifferentiated state, may also do the same for adipose-derived SP cells.

The adipose-derived stem cell side population (ADSC-SP) is a cell population found within adipose tissue that is pluripotent and suitable for use in tissue regeneration applications.

The term "adipose-derived stem cell" refers to a population of adipose cells found in post-natal mammals that are pluripotent and have the potential to differentiate into a variety of cell types. Adipose SP, adipose-derived SP and ADSC-SP cells all refer to the same subpopulation of ADSC that in humans have the phenotype $Lin^-$, $Sca-1^+$, $CD90^+$, $CD34^{+/low}$, $CD13^{+/low}$, $CD117^-$ and $CD18^{+/low}$. Any embodiment which discloses the use of ADSC can be performed with ADSC-SP and any embodiment which discloses using ADSC-SP can be performed with ADSC.

The SP phenotype of ADSC-SP was inhibited by verapamil, suggesting that the Hoechst dye exclusion phenomenon is due to ATP Binding Cassette (ABC) transporters. Recent studies showed that the expression of one ABC transporter, the breast cancer resistance protein 1 (Bcrp1) gene, is common to stem cells which reside in bone marrow, skeletal muscle, gonad tissue, mammary tissue, liver, prostate glands, and the retina. Collectively, these studies demonstrate that tissues contain their own subpopulation of adult stem cells that contribute to tissue repair and maintenance. Also, this may suggest that adult stem cells may share a common progenitor cell that, perhaps during development, migrated to all tissue types while preserving pluripotent characteristics.

Additionally, the present inventors demonstrated that adipose SP cells have the capability to differentiate into osteogenic, chondrogenic, neurogenic, and adipogenic cells. Bulk isolation of adipose-derived stem cells can differentiate into multiple mesenchymal lineages. Adipose-derived SP cells may be adipose precursor cells with a high degree of plasticity and lay quiescent until some signal stimulates them to commit to a specific lineage in response to apoptosis, cellular damage, or for tissue homeostasis.

Previously the characterization and isolation of ADSC-SP cells has been difficult. Therefore, the present inventors have developed a method to isolate ADSC-SP. Defined markers of bone marrow SP cells were used to determine if bone marrow- and adipose-derived SP cells share common characteristics. Adipose SP cells were found to be lineage negative ($Lin^-$). The lineage cocktail of antibodies identifies precursor cells committed to various hematopoetic lineages. Lineage is define for murine cells as expressing the markers CD3e, CD11c, CD45R/B220, Ly-76, Ly-6G and Ly-6C and for human cells, expressing the markers CD2, CD3, CD14, CD16, CD19, CD24, CD56, CD66b and glycophorin A. Adipose stem cells can reconstitute peripheral blood in mice, demonstrating the high plasticity of adipose stem cells. Since adipose-derived SP cells did not stain for any lineage markers, adipose-derived SP cells exist in an undifferentiated state.

Additionally, other cell surface markers common to hematopoetic stem cells (HSCs) were examined. Adipose SP cells were CD34 positive, but the expression was low. Over 80% of adipose SP cells expressed the phenotype $Sca-1/Lin^-$, which is associated with hematopoietic progenitors. Adipose SP cells were found to be $CD90^+$, $CD13^{+/low}$, and $CD117^-$. Interestingly, CD117 was not expressed on adipose-derived SP cells. This marker is common to HSC and the absence on adipose-derived SP cells may suggest some type of developmental divergence during organogenesis. The overall phenotype for murine adipose-derived SP cells is $Lin^-$, $Sca-1^+$, $CD90^+$, $CD34^{+/low}$, $CD13^{+/low}$, and $CD117^-$. The overall phenotype for human adipose-derived SP cells is $Lin^-$, $Sca-1^+$, $CD90^+$, $CD34^{+/low}$, $CD13^{+/low}$, $CD117^-$ and $CD18^{+/low}$.

Adipose-derived SP cells, isolated from mouse adipose tissue and sorted into culture, remain undifferentiated, are in a quiescent state, retain a high level of plasticity in vitro and have the ability to differentiate into different cell types in vitro. The phenotype of adipose-derived SP cells is similar to HSC and therefore adipose-derived SP cells may be derived from a common progenitor cell that other stem cells, such as HSCs, may be related to.

In one embodiment of the present invention, ADSC-SP cells are isolated from adipose tissue by a method comprising obtaining adipose tissue from a mammal, forming a cell suspension of adipose cells from the adipose tissue, staining the adipose cells with Hoechst 33342 dye and isolating a side population of cells from the Hoechst-stained adipose cells that is $Lin^-$, $Sca-1^+$, $CD90^+$, $CD34^{+/low}$, $CD13^{+/low}$, $CD117^-$ and $CD18^{+/low}$.

Figure 6:
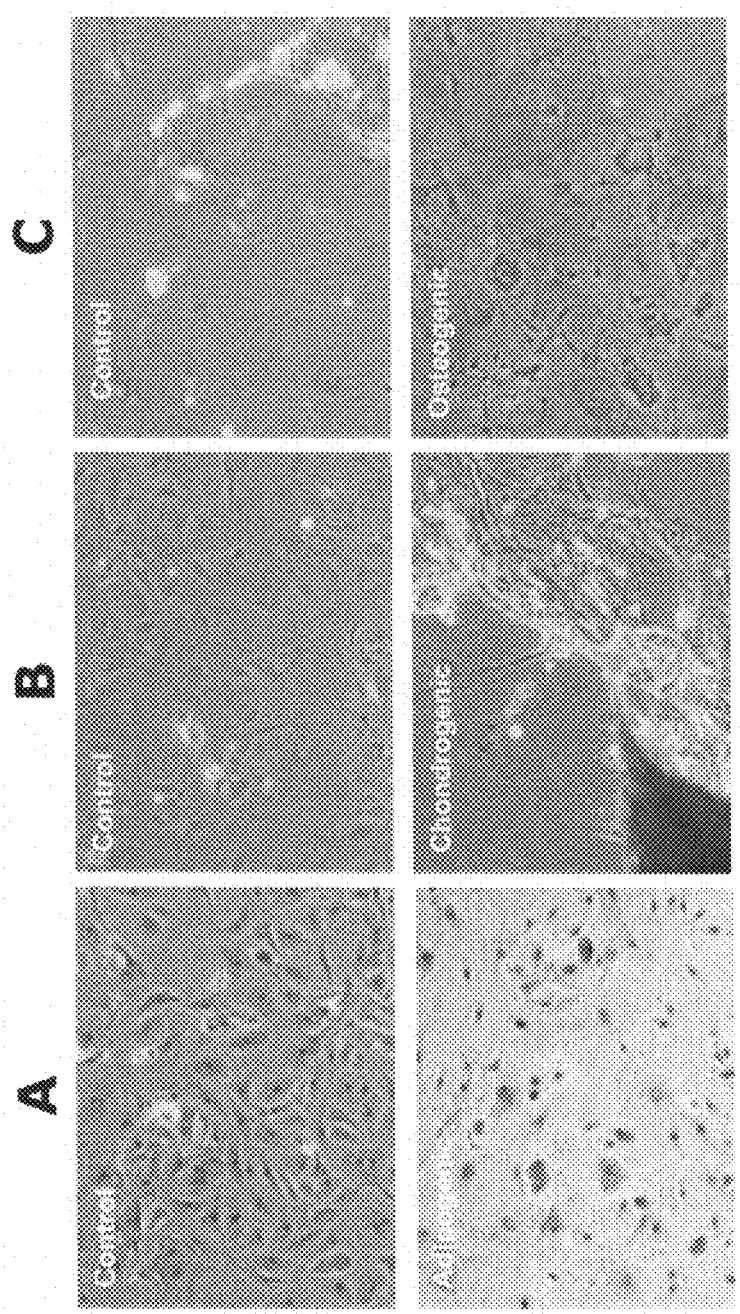
FIG. 6 depicts morphogenic differentiation of murine ADSC-SP cells into adipogenic cells, chondrogenic cells and osteogenic cells according to the teachings of the present invention.

The adipose-derived stem cell side population cells are particularly suitable for use in tissue regeneration. Adipose-derived stem cell side population cells have the ability to differentiation into cells of a variety of lineages including, but not limited to, the adipogenic, chondrogenic, osteogenic, neurogenic and cardiogenic lineages as demonstrated in Example 3 and FIGS. 6 and 7.

In particular, the ADSC-SP cells of the present invention are suitable for treatment of wounds to induce tissue regeneration and healing without the formation of scar tissue. These ADSC-SP cells present an improvement over existing therapies in that they can be harvested from the mammal to be treated and can be used for tissue regeneration of a variety of tissue injuries or defects.

Embodiments of the present invention provide compositions and methods for tissue regeneration of skin at the site of a wound. A wound occurs when the structure and/or integrity of tissues are compromised, for example when skin breaks, muscles tear or die, a bone is fractured or the tissue is burned. A wound may be caused by accidents, trauma or a medical procedure, by an infectious disease or an underlying disease condition. Depending on the location, extent and severity of a wound it can be classified as closed or open.

The present invention provides ADSC and ADSC-SP for tissue regeneration. In an embodiment of the present invention, the adipose-derived stem cells are autologous. In a non-limiting example, approximately 0.5 to approximately 5.0× $10^6$ adipose-derived stem cells/10 mm of treatment site per treatment site per day, are intradermally injected adjacent to the treatment site. The adipose-derived stem cells aid in wound healing by increasing vaspularization, increasing cell migration to the site of injury, decreasing the amount of scarring and increasing tissue regeneration. Adipose-derived stem cells also decrease the healing time of wounds, thereby decreasing the possibility of infection. There are cosmetic, as well as medical, benefits such as reduced scarring resulting from open or closed wound treatment. In addition, embodiments of the present invention aid in wound healing in patients with chronic diseases such as diabetes.

The adipose-derived stem cells of the present invention provide tissue regeneration for the treatment of both acute and chronic wounds. Acute wounds are those wounds that heal promptly, within 30 days (or 60 days in diabetics). Non-limiting examples of acute wounds that can be treated with the present invention include abrasions, avulsions, contusions, crush wounds, cuts, lacerations, projectile wounds and puncture wounds. Chronic wounds include, but are not limited to, diabetic skin sores, pressure sores, surgical wounds, spinal injury wounds, burns, chemical-induced wounds and wounds due to blood vessel disorders.

An advantage of the present invention is that wound healing with adipose-derived stem cells results in wound healing by regeneration of like tissues rather than scar formation.

In an embodiment of the present invention, the adipose-derived stem cell is differentiated prior to use in tissue regeneration. In a non-limiting example, for tissue regeneration of cardiac tissue after myocardial infarction, it is possible to differentiate the adipose-derived stem cells into a cardiogenic precursor cell or cardiomyocyte prior to transplantation of the cells to the treatment site.

The present inventive method also can involve the co-administration of bioactive agents with the ADSC cells. By "co-administration" is meant administration before, concurrently with, e.g., in combination with bioactive agents in the same formulation or in separate formulations, or after administration of a therapeutic composition as described above.

As used herein, the phrase, "bioactive agents" refers to any organic, inorganic, or living agent that is biologically active or relevant. For example, a bioactive agent can be a protein, a polypeptide, a polysaccharide (e.g. heparin), an oligosaccharide, a mono- or disaccharide, an organic compound, an organometallic compound, or an inorganic compound. It can include a living or senescent cell, bacterium, virus, or part thereof. It can include a biologically active molecule such as a hormone, a growth factor, a growth factor producing virus, a growth factor inhibitor, a growth factor receptor, an anti-inflammatory agent, an antimetabolite, an integrin blocker, or a complete or partial functional insense or antisense gene. It can also include a man-made particle or material, which carries a biologically relevant or active material. An example is a nanoparticle comprising a core with a drug and a coating on the core.

Bioactive agents also can include drugs such as chemical or biological compounds that can have a therapeutic effect on a biological organism. Non-limiting examples include, but are not limited to, growth factors, anti-rejection agents, anti-inflammatory agents, anti-infective agents (e.g., antibiotics and antiviral agents), analgesics and analgesic combinations, anti-asthmatic agents, anticonvulsants, antidepressants, anti-diabetic agents, anti-neoplastics, anticancer agents, anti-psychotics, antioxidants, immunosuppressive agents, vitamins and minerals, and agents used for cardiovascular diseases such as anti-restenosis and anti-coagulant compounds.

Bioactive agents also can include precursor materials that exhibit the relevant biological activity after being metabolized, broken-down (e.g. cleaving molecular components), or otherwise processed and modified within the body. These can include such precursor materials that might otherwise be considered relatively biologically inert or otherwise not effective for a particular result related to the medical condition to be treated prior to such modification.

Combinations, blends, or other preparations of any of the foregoing examples can be made and still be considered bioactive agents within the intended meaning herein. Aspects of the present invention directed toward bioactive agents can include any or all of the foregoing examples.

In one embodiment of the present invention, the bioactive agent is a growth factor. A growth factor is any agent which promotes the proliferation, differentiation and functionality of implanted ADSC. Non-limiting examples of suitable growth factors include leukemia inhibitory factor (LIF), epidermal growth factor (EGF), fibroblast growth factor (FGF), transforming growth factor-beta (TBF-β), insulin-like growth factor (IGF), and vascular endothelial growth factor (VEGF), human growth hormone, platelet-derived growth factor (PDGF), interleukins, cytokines or combinations thereof.

In one embodiment of the present invention, the bioactive agent is an immunosuppressive agent. An immunosuppressive agent is an agent is any agent which prevents, delays the occurrence of or decreases the intensity of the desired immune response, e.g., rejection of a transplanted cell, tissue, or organ.

As used herein, "immunosuppression" refers to prevention of the immune response (for example by the administration of an "immunosuppresive agent", as defined herein) such that an "immune response", as defined herein, is not detectable. As used herein, "prevention" of an immune response means an immune response is not detectable. An immune response (for example, transplant rejection or antibody production) is detected according to methods well-known in the art and defined herein.

"Immunosuppression" according to the invention also means a delay in the occurrence of the immune response as compared to any one of a transplant recipient that has not received an immunosuppresive agent, or a transplant recipient that has been transplanted with material that is not "immunologically blinded" or "immunoprivileged", as defined herein. A delay in the occurrence of an immune response can be a short delay, for example 1 hr-10 days, i.e., 1 hr, 2, 5 or 10 days. A delay in the occurrence of an immune response can also be a long delay, for example, 10 days-10 years (i.e., 30 days, 60 days, 90 days, 180 days, 1, 2, 5 or 10 years).

"Immunosuppression" according to the invention also means a decrease in the intensity of an immune response. According to the invention, the intensity of an immune response can be decreased such that it is 5-100%, preferably, 25-100% and most preferably 75-100% less than the intensity of the immune response of any one of a transplant recipient that has not received an immunosuppresive agent, or a transplant recipient that has been transplanted with material that is not autologous. The intensity of an immune response can be measured by determining the time point at which transplanted material is rejected. For example, an immune response comprising rejection of transplanted material at day 1, post-transplantation, is of a greater intensity than an immune response comprising the rejection of transplanted material at day 30, post-transplantation. The intensity of an immune response can also be measured by quantitating the amount of a particular antibody capable of binding to the transplanted material, wherein the level of antibody production correlates directly with the intensity of the immune response. Alternatively, the intensity of an immune response can be measured by determining the time point at which a particular antibody capable of binding to the transplanted material is detected.

Various strategies and agents can be utilized for immunosuppression. For example, the proliferation and activity of lymphocytes can be inhibited generally with agents such as, for example, FK-506, or cyclosporin or other immunosuppressive agents. Another possible strategy is to administer an antibody, such as an anti-GAD65 monoclonal antibody, or another compound which masks a surface antigen on a transplanted cell and therefore renders the cell practically invisible to the immune system of the host.

An "immunosuppressive agent" is any agent that prevents, delays the occurrence of or reduces the intensity of an immune reaction against a foreign cell in a host, particularly a transplanted cell. Preferred are immunosuppressive agents which suppress cell-mediated immune responses against cells identified by the immune system as non-self. Examples of immunosuppressive agents include, but are not limited to, cyclosporin, cyclophosphamide, prednisone, dexamethasone, methotrexate, azathioprine, mycophenolate, thalidomide, FK-506, systemic steroids, as well as a broad range of antibodies, receptor agonists, receptor antagonists, and other such agents as known to one skilled in the art.

In yet another embodiment of the present invention, adipose-derived stem cells are administered with hyperbaric oxygen therapy for the treatment of chronic wounds.

In an embodiment of the present invention, adipose-derived stem cells are administered with skin grafts to aid in the grafting process and with tissue regeneration.

Adipose-derived stem cells or differentiated cells may be transplanted into the recipient where the cells will proliferate and differentiate to form new cells and tissues thereby providing the physiological processes normally provided by that tissue. The term "transplanted" as used herein refers to transferring cells alone or cells that are embedded in a support matrix. As used herein, the term "tissue" refers to an aggregation of similarly specialized cells united in the performance of a particular function. Tissue is intended to encompass all types of biological tissue including both hard and soft tissue. Soft tissue refers to tissues that connect, support, or surround other structures and organs of the body. Soft tissue includes muscles, tendons (bands of fiber that connect muscles to bones), fibrous tissues, fat, blood vessels, nerves, and synovial tissues (tissues around joints). Hard tissue includes connective tissue (e.g., hard forms such as osseous tissue or bone) as well as other muscular or skeletal tissue.

In another embodiment of the present invention, the ADSC are administered with a pharmaceutically acceptable carrier or excipients. The pharmaceutically acceptable excipients described herein, for example, vehicles, adjuvants, carriers or diluents, are well-known to those who are skilled in the art and are readily available to the public. It is preferred that the pharmaceutically acceptable carrier or excipient be one which is chemically inert to the therapeutic composition and one which has no detrimental side effects or toxicity under the conditions of use.

The choice of excipient or carrier will be determined in part by the particular therapeutic composition, as well as by the particular method used to administer the composition. Accordingly, there are a wide variety of suitable formulations of the pharmaceutical composition of the present invention. The formulations described herein are merely exemplary and are in no way limiting.

Often the physiologically acceptable carrier is an aqueous pH buffered solution. Examples of physiologically acceptable carriers include, but are not limited to, saline, solvents, dispersion media, cell culture media, aqueous buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The present invention further provides therapeutic compositions useful in practicing the therapeutic methods of this invention. A subject therapeutic composition includes, in admixture, a pharmaceutically acceptable excipient (carrier) or media and the ADSC of the present invention, including cells or tissues derived therefrom, alone or in combination with one or more bioactive agents, and at a strength effective for administration by various means to a patient experiencing cellular or tissue loss or deficiency.

It is a still further embodiment of the present invention to provide therapeutic compositions for use in methods which comprise or are based upon the ADSC of the present invention, including lineage-uncommitted populations of cells, lineage-committed populations of cells or tissues derived therefrom, along with a pharmaceutically acceptable carrier or media. Also contemplated are therapeutic compositions comprising bioactive agents that act on or modulate the ADSC of the present invention and/or the cells or tissues derived therefrom, along with a pharmaceutically acceptable carrier or media.

The preparation of cellular or tissue-based therapeutic compositions is well understood in the art. Such compositions may be formulated in a pharmaceutically acceptable media. The cells may be in solution or embedded in a matrix. The preparation of therapeutic compositions with bioactive agents (such as, for example, growth factors) as active ingredients is well understood in the art. The active therapeutic ingredient is often mixed with excipients or media which are pharmaceutically acceptable and compatible with the active ingredient. In addition, if desired, the composition can contain minor amounts of auxiliary substances such as wetting or emulsifying agents, pH buffering agents which enhance the effectiveness of the active ingredient.

A bioactive agent can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions of the present invention are administered in a manner compatible with the dosage formulation, and in a therapeutically effective amount. The quantity to be administered depends, for instance, on the subject and debilitation to be treated, capacity of the subject's organ, cellular and immune system to accommodate the therapeutic composition, and the nature of the cell or tissue therapy, etc. Precise amounts of therapeutic composition required to be administered depend on the judgment of the practitioner and are peculiar to each individual. However, suitable dosages of the therapeutic composition of the present invention may range from about $0.05\text{-}100.0\times10^6$ adipose-derived stem cells/ 10 mm of treatment site per treatment site per day cells per treatment site per day, preferably about $0.10\text{-}50.0\times10^6$ adipose-derived stem cells/10 mm of treatment site per treatment site per day cells per treatment site per day, and more preferably about 0.5-5.0×10⁶ adipose-derived stem cells/10 mm of treatment site per treatment site per day, and depend on the route of administration and the size of the treatment site. Suitable regimes for initial administration and follow on administration are also variable, but can include an initial administration followed by repeated doses at one or more hour, or day, intervals by a subsequent injection or other administration.

One of skill in the art may readily determine the appropriate concentration of cells for a particular purpose. An exemplary dose is in the range of about 0.05-100.0×10⁶ cells per treatment site per day. In a non-limiting example, approximately 0.5×10⁶ adipose-derived stem cells/10 mm of treatment site per treatment site per day, are intradermally injected adjacent to, or within, the treatment site.

In another embodiment of the present invention, ADSC are administered to the treatment site of a mammal at any time after the appearance of a wound or an injury when tissue regeneration is needed. Precise administration schedules for the therapeutic composition depend on the judgment of the practitioner and the type and extent of the wound or injury and are peculiar to each individual.

The ADSC or differentiated cells of the present invention can be administered by injection into a target site of a subject, preferably via a delivery device, such as a tube, e.g., catheter. In one embodiment, the tube additionally contains a needle, e.g., a syringe, through which the cells can be introduced into the subject at a desired location. Specific, non-limiting examples of administering cells to subjects may also include administration by subcutaneous injection, intramuscular injection, or intravenous injection. If administration is intravenous, an injectable liquid suspension of cells can be prepared and administered by a continuous drip or as a bolus.

Cells may also be inserted into a delivery device, e.g., a syringe, in different forms. For example, the cells can be suspended in a solution contained in such a delivery device. As used herein, the term "solution" includes a pharmaceutically acceptable carrier or diluent in which the cells of the invention remain viable. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating ADSC or differentiated cells as described herein, in a pharmaceutically acceptable carrier or diluent and, as required, other ingredients enumerated above, followed by filter sterilization.

The cells may be administered systemically (for example intravenously) or locally (for example directly into a myocardial defect under echocardiogram guidance, or by direct application under visualization during surgery). For such injections, the cells may be in an injectable liquid suspension preparation or in a biocompatible medium which is injectable in liquid form and becomes semi-solid at the site of damaged tissue. A conventional intra-cardiac syringe or a controllable endoscopic delivery device can be used so long as the needle lumen or bore is of sufficient diameter (e.g. 30 gauge or larger) that shear forces will not damage the cells being delivered.

Cells may be administered in any manner that permits them to graft to the intended tissue site and reconstitute or regenerate the functionally deficient area.

Support matrices into which the ADSC can be incorporated or embedded include matrices which are biocompatible, recipient-compatible and which degrade into products which are not harmful to the recipient. These matrices provide support and protection for ADSC and differentiated cells in vivo.

Natural and/or synthetic biodegradable matrices are examples of such matrices. Natural biodegradable matrices include plasma clots, e.g., derived from a mammal, collagen, fibronectin, and laminin matrices. Suitable synthetic material for a cell transplantation matrix must be biocompatible to preclude migration and immunological complications; and should be able to support extensive cell growth and differentiated cell function. It must also be resorbable, allowing for a completely natural tissue replacement. The matrix should be configurable into a variety of shapes and should have sufficient strength to prevent collapse upon implantation. Recent studies indicate that the biodegradable polyester polymers made of polyglycolic acid fulfill all of these criteria, as described by Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991). Other synthetic biodegradable support matrices include synthetic polymers such as polyanhydrides, polyorthoesters, and polylactic acid. Further examples of synthetic polymers and methods of incorporating or embedding cells into these matrices are also known in the art. See e.g., U.S. Pat. Nos. 4,298,002 and 5,308,701.

Attachment of the cells to the polymer may be enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture. All polymers for use in the matrix must meet the mechanical and biochemical parameters necessary to provide adequate support for the cells with subsequent growth and proliferation.

One of the advantages of a biodegradable polymeric matrix is that angiogenic and other bioactive compounds can be incorporated directly into the support matrix so that they are slowly released as the support matrix degrades in vivo. As the cell-polymer structure is vascularized and the structure degrades, placental stem cells may differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, bioactive agents which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), epidermal growth factor (EGF), and heparin binding epidermal growth factor like growth factor (HB-EGF), could be incorporated into the matrix or provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792, 525, 5,965,997, 4,879,237 and 4,789,734).

In another example, the cells may be transplanted in a gel matrix (such as Gelfoam from Upjohn Company) which polymerizes to form a substrate in which the placental stem cells or differentiated cells can grow. A variety of encapsulation technologies have been developed (e.g. Lacy et al., Science 254:1782-84 (1991); Sullivan et al., Science 252:718-

712 (1991); WO 91/10470; WO 91/10425; U.S. Pat. No. 5,837,234; U.S. Pat. No. 5,011,472; U.S. Pat. No. 4,892,538). During open surgical procedures, involving direct physical access to the damaged tissue and/or organ, all of the described forms of undifferentiated placental stem cells or differentiated placental stem cell delivery preparations are available options. These cells can be repeatedly transplanted at intervals until a desired therapeutic effect is achieved.

In an exemplary embodiment, a therapeutic composition comprising an effective amount of ADSC may be used to treat a subject with a vascular disease. As used herein, "vascular disease" refers to a disease of the human vascular system. Examples include peripheral arterial disease, abdominal aortic aneurysm, carotid disease, and venous disease. The ADSCs can be used to produce vascular endothelial cells that may be used in methods for remodeling tissue or replacing a scar tissue in a subject. Vascular endothelial cells may also be used to repair vascular damage.

EXAMPLES

Example 1

Generation and Culture of Adipose-Derived Stem Cells

This example demonstrates the isolation of adipose-derived stem cells. While the following example described the isolation of adipose-derived stem cells from mouse tissue, it would be possible for a person of ordinary skill in the art to use these techniques to isolate adipose-derived stem cells from other mammalian tissues.

Briefly, visceral fat encasing the stomach and intestines was removed and finely minced with sterile scissors. The dissected fat was then washed ten times with calcium/magnesium-free Dulbecco's phosphate-buffered saline containing 1 mM EDTA (DPBS(−)/EDTA) and centrifuged at 500 xg for 5 min after each wash step to remove floating adipocytes. The adipose tissue was then incubated in DPBS(−)/EDTA for ten minutes at room temperature and the adipose tissue was then mechanically disaggregated with surgical scissors or with a BD Medimachine (BD Biosciences, San Jose, Calif.). The disaggregated adipose tissue was then enzymatically digested with type I collagenase (0.075%, Sigma) for 15 min at 37° C. The adipose tissue was then further digested with trypsin/EDTA for 15 min at 37° C. The digestion was stopped by addition of an equal volume of DMEM culture medium containing 10% FBS. The digested adipose tissues was then washed with DMEM/10% FBS by centrifuging at 350 xg for 5 min for each wash. The pellet was then resuspended in DMEM/10% FBS and filtered through a 70 µm nylon mesh. The adipose-derived stem cells were then resuspended in DMEM/10% FBS/1× non-essential amino acids/1× antibiotic/antimycotic (basal media).

The adipose-derived stem cells isolated above were then maintained in basal media, fed every other day and passaged when they reached approximately 80% confluency. At each passage the cells were split 1:2 such that the cell reach confluency every 2 days. The cells are cultured to passage four and then used for differentiation, transplanted into a patient or cryopreserved for transplant at a later date.

Example 2

Identification of Adipose-Derived Stem Cell Side Population Cells

For adipose-derived stem cell side population cell (ADSC-SP) analysis, adipocytes were suspended in a concentration of $1 \times 10^6$ cells/mL in DMEM with 10% FBS. The cells were incubated with Hoechst 33342 (Sigma) at a final concentration of 2.5 µg/mL. The cells were gently agitated every 20 min in a 37° C. water bath for a total of 90 min. After incubation, cells were pelleted by centrifugation and kept on ice until flow sorting. To demonstrate Hoechst efflux inhibition, cells were incubated with verapamil (Sigma) at a final concentration of 25 µg/mL in addition to Hoechst staining for the same incubation period.

Sorting was done on a Cytopeia InFlux Cell Sorter (Seattle, Wash.). Hoechst-stained cells were excited with a 355 nm 20 mW UV laser (Lightwave Electronics, Mountain View, Calif.) and Hoechst blue and red emission was separated with a 560 nm dichroic mirror and collected using a 460/50 and 670/40 band pass filters, respectively. Fluorescein isothiocyanate (FITC) and phycoerythrin (PE) were excited with a 488 nm 200 mW laser (Coherent, Santa Clara, Calif.) and emission was collected with a 530/40 and 580/30 band pass filters, respectively. Allophycocyanin (APC) was excited with a 638 nm 25 mW laser (Coherent) and emission was collected with a 670/40 band pass filter.

For antibody staining, cells were spun down and concentrated into 500 mL of Hoechst staining buffer and kept on ice. Cells were stained with anti-mouse Sca-1-PE, CD90-APC, CD117-APC, CD34-FITC, and antibodies for lineage determination (BD Biosciences Pharmingen, San Diego, Calif.). The lineage kit contains anti-mouse CD3e, CD11c, CD45R/B220, Ly-76, Ly-6G and Ly-6C all conjugated to APC. Cells were stained for 30 minutes, washed once in cold Hoechst staining buffer and kept on ice until flow analysis.

The staining conditions used to identify side population cells in other tissues were applied to a single cell suspension of enzymatically digested adipose tissue. The conserved phenomenon of Hoechst 33342 efflux was also observed in adipose tissue. The frequency of the adipose side population cells was 1.5%±0.5% (mean±sd, n=4). To identify the side population cells, all scatter events were included in the first gate of the scatter plot. Adipose-derived stem cell SP cells, identified by Hoechst staining, were backgated on the scatter plot. Digested adipose tissue shows three major populations of cells on the scatter plot. Adipose-derived stem cell SP cells appear to reside in an area related to low side scatter (SSC) and low to mid forward scatter (FSC) (FIG. 1). Adipose-derived stem cell SP cells have a low SSC, indicating they are smaller than the main population of cells.

Figure 2:
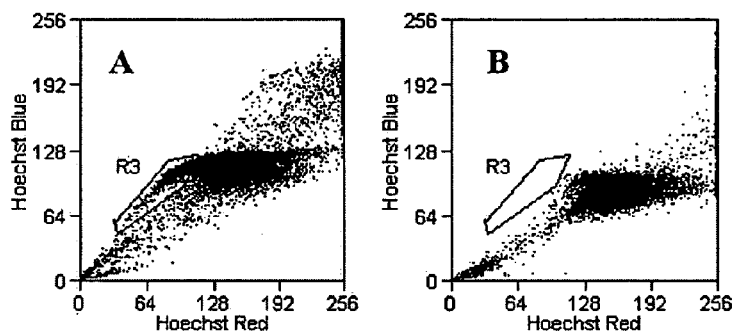
FIG. 2 depicts the flow cytometric analysis of verapamil-treated murine ADSC-SP cells with inhibited Hoechst 33342 efflux according to the teachings of the present invention.

The SP phenotype in many tissues is caused by membrane bound protein transporters of the ABC transporter superfamily. To determine whether ABC transporter activity creates the SP phenotype in ADSC-SP cells, verapamil was added to the cell suspension to a final concentration of 25 µg/mL (FIG. 2). The addition of verapamil diminished the efflux of Hoechst dye suggesting that the SP phenotype is due to the ABC transporter.

Adipose-derived stem cell SP cells were stained for surface markers common to many types of side population cells. All markers were direct conjugated antibodies studied with flow cytometry. Negative controls were unstained adipose cells. Positive staining was defined as fluorescence intensity above 95% of the negative control. Staining not as intense, falling in a range of 30%-80%, was considered low to mid level staining.

Figure 3:
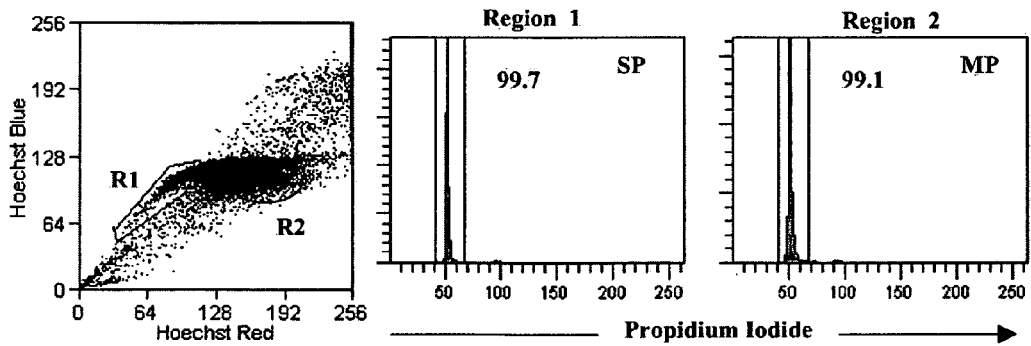
FIG. 3 depicts cell cycle analysis of murine ADSC-SP cells according to the teachings of the present invention.

Adult stem cells, under tight regulatory control, are mainly quiescent during their life cycle. Freshly sorted adipose side population cells were stained with propidium iodide to assess their cell cycle status. The data indicates that both the side population and the main population cells are mainly quiescent, with less than 0.5% of the cells in growth phase. This was also true for other cells that stained with Hoechst 33342 at a greater intensity (FIG. 3).

Figure 4:
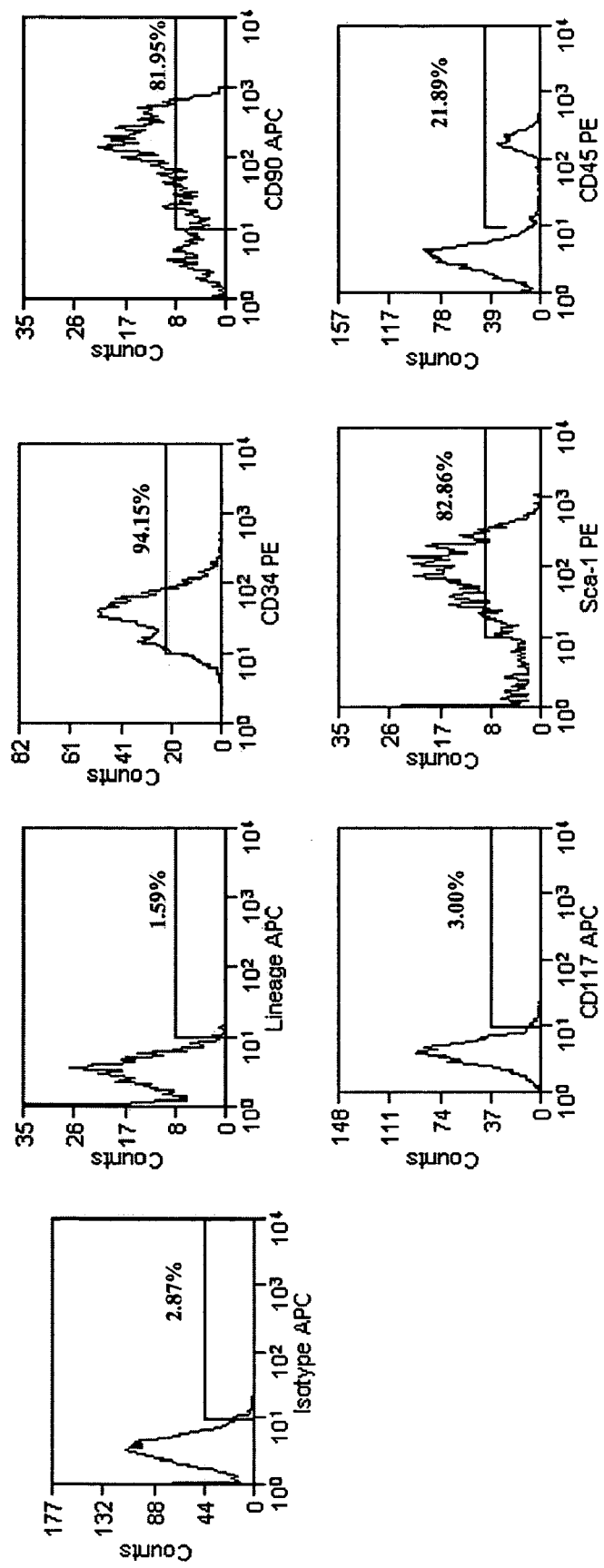
FIG. 4 depicts cell surface marker characterization of murine ADSC-SP cells according to the teachings of the present invention.

Adipose-derived stem cell SP cells are cells that efflux Hoechst 33342 dye and are enriched for stem cells. However, not all ADSC-SP cells express stem cell markers. The ADSC-SP cell population contains cells that have not committed to any lineage. This is evidenced by the absence of any staining of lineage specific antibodies. Stem cell antigen-1 (Sca-1) is expressed on 81+/−5% of ADSC-SP cells. Similarly, CD90 was expressed on 80% of ADSC-SP cells. A multivariate plot shows that 75+/−7% of ADSC-SP cells have both Sca-1 and CD90 (FIG. 4). Adipose-derived stem cell SP cells stained low for CD34 and CD13. CD117, which is important for development of many stem cells, was not expressed on ADSC-SP cells (FIG. 4).

Example 3

Differentiation of ADSC-SP Cells

Figure 5:
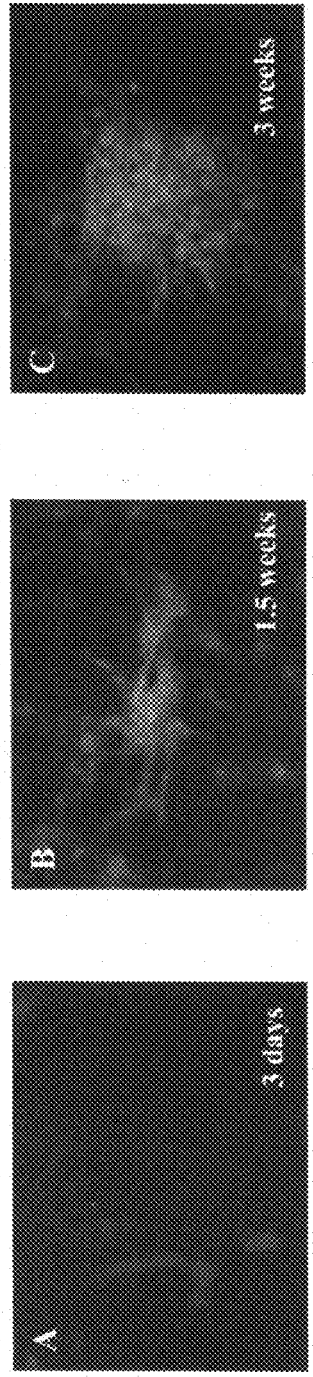
FIG. 5 depicts the characteristics of murine ADSC-SP cells after three days (A), 1.5 weeks (B) and three weeks (C) in culture according to the teachings of the present invention.

After sorting, cells were washed once with DMEM supplemented with 10% FBS and cultured on a feeder layer of mouse embryonic fibroblast STO cells. The STO feeder cells were plated on dishes coated with 0.1% (wt/vol) gelatin, treated with mitomycin C (Sigma) at a concentration of 10 μg/ml for 2.5 h at 37° C., and washed three times with PBS. Sorted ADSC-SP cells were plated onto mitomycin C-treated STO feeder cells with a daily change of culture medium (FIG. 5).

To examine the functional capabilities of ADSC-SP cells, they were differentiated into different cell types. For osteogenesis, adipogenesis, and neurogenesis 50,000 cultured ADSC-SP cells at passage four were plated. For chondrogenesis, 80,000 cultured ADSC-SP cells at passage four were plated as a micromass.

Adipogenesis

Fifty thousand cells were grown in adipogenic induction and maintenance medium (Cambrex, Walkersville, Md.) according to manufacturer's specifications. Briefly, cells were plated into a 6 cm dish in DMEM with 10% FBS and allowed to attach. Cells were transferred into adipogenic induction medium for 3 days and changed to adipogenic maintenance medium for 3 days. ADSC-SP cells were cultured in adipogenic medium for three rounds days until fat vacuoles developed. The earliest time in which vacuoles were evident was at 7-10 days. Approximately 50-60% of the ADSC-SP cells developed fat vacuoles. As the cells became larger, the most obvious morphological change was the appearance of fat vacuoles.

Cells cultured in adipogenic medium were then stained for adipogenic changes. Cells were washed 2× in PBS and fixed in 4% paraformaldehyde overnight at 4° C. Plates were washed three times in 70% ethanol and incubated with oil red O staining dye for 5 minutes at room temperature. Plates were washed three times with 70% ethanol and twice with $dH_2O$ to remove excess dye. Hematoxylin was added to visualize cell nuclei for 5 minutes. Plates were washed with $dH_2O$ twice. Staining with oil red O showed cells with oil droplets as a deep red color (FIG. 6A). The control dish had no staining for oil red.

Chondrogenesis

Eighty thousand cells were grown in chondrogenic induction medium (Cambrex) according to manufacturer's specifications. Briefly, cells were pelleted into a micromass in 100 μL of DMEM with 10% FBS and were allowed to attach tightly into a micromass plated in the center of a 6 cm dish. Cells were cultured with chondrogenic induction medium that was changed every two days. While in chondrogenic medium, morphological changes began as early as 5 days. The cells enlarged and the micromass had become much more dense. At days 7-8 the micromass condenced into a visible pellet and lifted off the culture dish.

At this point the cells were stained with alcian blue reagent to detect proteoglycosylations. Cells were washed 2× in PBS and fixed in 4% paraformaldehyde overnight at 4° C. Cells were incubated with 1% (w/v) alcian blue in 0.1N HCl. Plates were incubated at room temperature for 1 hour. Plates were washed three times with 0.1N HCl to remove excess dye. The entire micromass stained deep blue and the surrounding cells also stained blue in their cytoplasm (FIG. 6B). The control dish had little to no staining.

Osteogenesis

Fifty thousand cells were grown in osteogenic induction medium (Cambrex) according to manufacturer's specifications. Briefly, cells were plated into a 6 cm dish in DMEM with 10% FBS and allowed to attach. Cells were cultured with osteogenic induction medium that was changed every two days. Osteogenis morphological changes began showing after 10-14 days in culture. Adipose SP cells had become large and cuboidal while undergoing osteogenesis.

After 21 days of culture, osteogenic cells were stained with von Kossa reagent to identify calcified deposits which signify early osteogenesis. Cells were washed 2× in PBS and fixed in 4% paraformaldehyde overnight at 4° C. Plates were washed 2× in $dH_2O$. Five percent silver nitrate (w/v) was added and the plates were exposed to UV light for 45-60 minutes. The plates were washed in $dH_2O$ until all the silver nitrate was removed. The plates were counterstained with 2% sodium thiosulfate for 5 minutes. Close to 90% of the cells stained with von Kossa (FIG. 6C).

Neurogenesis

Figure 7:
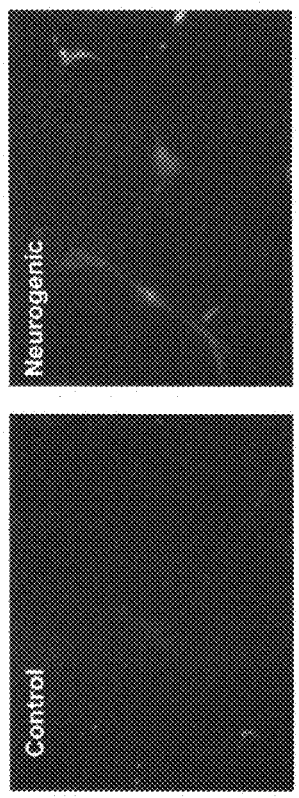
FIG. 7 depicts the morphological signs of neurogenesis in murine ADSC-SP cells after two days in culture according to the teachings of the present invention.

Fifty thousand cells were grown in DMEM with 20% FBS supplemented with 1 mM β-mercaptoethanol for a total of three days. Medium was changed daily. Morphological signs of neurogenesis were seen as early as two days after culturing. Neuron-like dendritic progections began to develop and the cell somas began to undertake pyrimadal morphology, a shape specific for neurons. After 3 days of culture, the cells were stained for nestin. Cells were washed twice in PBS and fixed in 4% paraformaldehyde overnight at 4° C. Plated were blocked for 30 minutes with Fc block (BD Pharmingen) diluted in PBS blocking buffer (1× PBS+10% FBS). Cells were washed three times in PBS-T wash buffer (1× PBS+ 0.1% Triton X-100) and were further incubated in PBS-T for 30 minutes. Mouse anti-nestin (IgG1), (Chemicon, Temecula, Calif.) was diluted in 1× PBS-T+2% FBS to a final dilution of 1:200 and incubated for 1 hour with constant rotation. Plated were washed twice in PBS-T. Anti-mouse immunoglobulin PE (BD Pharmingen) diluted 1:200 in PBS-T+2% FBS was incubated for 30 minutes for visualization. Approximately 70% of differentiated ADSC-SP cells expressed nestin (FIG. 7).

Cardiogenesis

Fifty thousand cells were grown in DMEM with 10% FBS supplemented with 5-azacytidine (Sigma) a final concentration of 9 mM. Cells were cultured for 3 days in cardiogenic induction medium then switched to DMEM with 10% FBS and stained for the cardiac marker troponin. Cells were washed 2× in PBS and fixed in 4% paraformaldehyde overnight at 4° C. Plates were blocked for 15 minutes with Fc block (BD Pharmingen) diluted in 1× PBS with 10% FBS. Cells were washed twice in PBS-T wash buffer (1× PBS+ 0.1% Triton X-100) and were further incubated in PBS-T for 30 minutes. Mouse anti-troponin1 (IgG2a), (Chemicon) was diluted in 1× PBS-T+2% FBS with a final dilution of 1:200 and incubated for 1 hour with constant rotation. Plates were washed twice in PBS-T. Anti-mouse Ig PE (BD Pharmingen) diluted 1:200 in PBS-T+2% FBS was incubated for 30 minutes for visualization.

Example 4

Isolation of Human ADSC-SP Cells

Adipose patches from human male gonad were placed in a 6 cm culture dish containing 1× PBS+0.01M EDTA, washed once and transferred to 10 cm dish with 1× PBS+0.01M EDTA. The tissue was minced into fine pieces and digested with an equal volume of 2 mg/mL collagenase I for 1 hour at 37° C. Following digestion, the adipose suspension was washed in DMEM-10 (DMEM+10% FBS+1% penicillin/ampicillin). Undigested adipose tissue was removed and the cell pellet was suspended in 5 mL of DMEM-10. The adipose cell suspension was then passed through a 100 µm filter mesh followed with a 70 µm mesh to remove large particles and clumps. The cells were counted and adjusted to be in a concentration of $1 \times 10^6$ cells per mL.

For SP analysis, human adipocytes were suspended in a concentration of $1 \times 10^6$ cells/mL in DMEM with 10% FBS. The cells were incubated with Hoechst 33342 (Sigma) at a final concentration of 5 µg/mL. The cells were gently agitated every 20 min in a 37° C. water bath for a total of 90 min. After incubation, cells were pelleted by centrifugation and kept on ice until flow sorting. To demonstrate Hoechst efflux inhibition, cells were incubated with verapamil (Sigma) at a final concentration of 25 µg/mL in addition to Hoechst staining for the same incubation period.

Sorting was done on a Cytopeia InFlux Cell Sorter (Seattle, Wash.). Hoechst-stained cells were excited with a 355 nm 20 mW UV laser (Lightwave Electronics, Mountain View, Calif.) and Hoechst blue and red emission was separated with a 560 nm dichroic mirror and collected using a 460/50 and 670/40 band pass filters, respectively.

Figure 8:
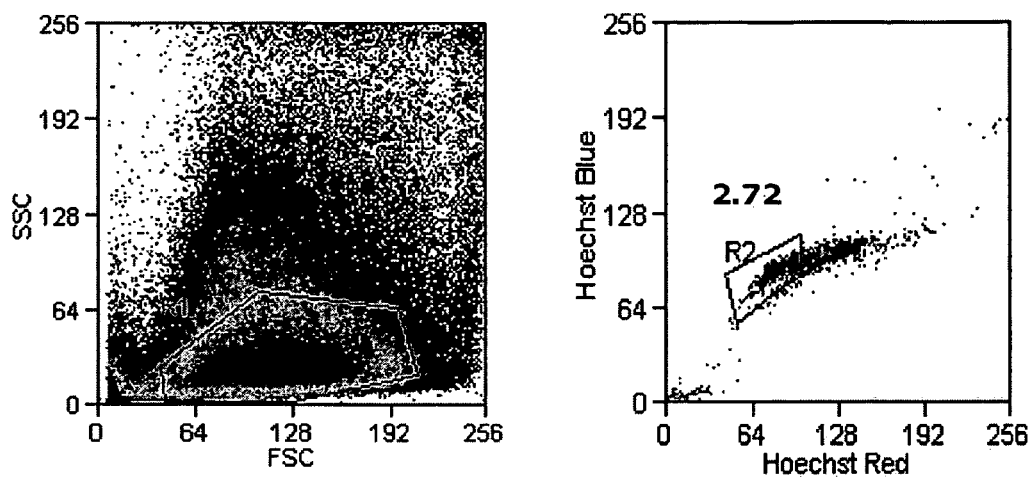
FIG. 8 depicts flow cytometric analysis of freshly isolated human adipose cells stained with Hoechst 33342 according to the teachings of the present invention.
Figure 9:
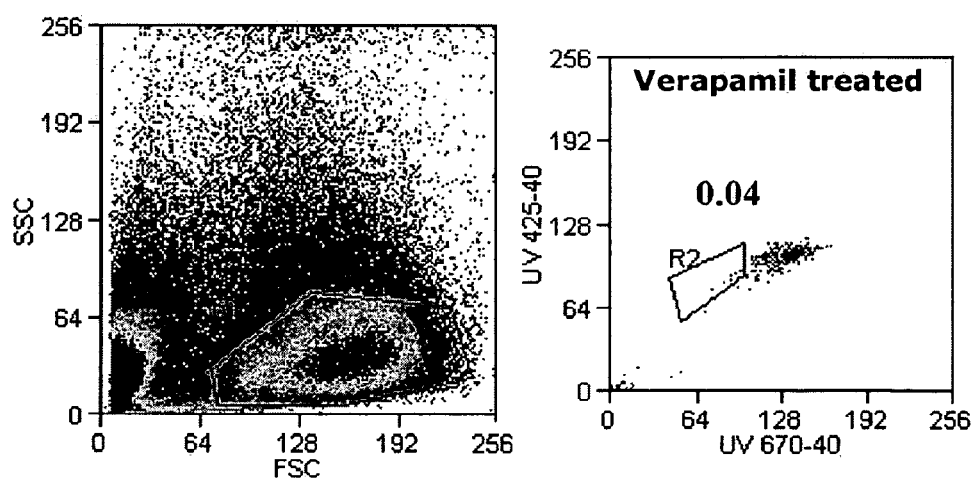
FIG. 9 depicts flow cytometric analysis of freshly isolated human adipose cells stained with Hoechst 33342 and verapamil according to the teachings of the present invention.

The conserved phenomenon of Hoechst 33342 efflux was observed in human adipose tissue. The frequency of the human ADSC-SP cells was 2.5%±0.5% (mean±sd, n=3). The human adipose cell suspension was homogeneous; most events in the scatter plot fell with the same area and the cells were gated to examine the Hoechst staining levels (R1). ADSC-SP cells, identified by a decreased level of Hoechst staining, were identified in the Hoechst blue vs. Hoechst red plot (FIG. 8). The adipose cells are a relatively homogeneous population consisting of one main cell type with SP cells as a minor population, only 2.72% of the cells gated in R1, the SP population. Verapamil (25 µg/mL final) was added to inhibit the Hoechst efflux to confirm the SP phenomenon. Consistent with previous results in mice, the SP was inhibited with the addition of verapamil (FIG. 9). Staining of cells without added verapamil causes the SP cells to return.

Figure 10:
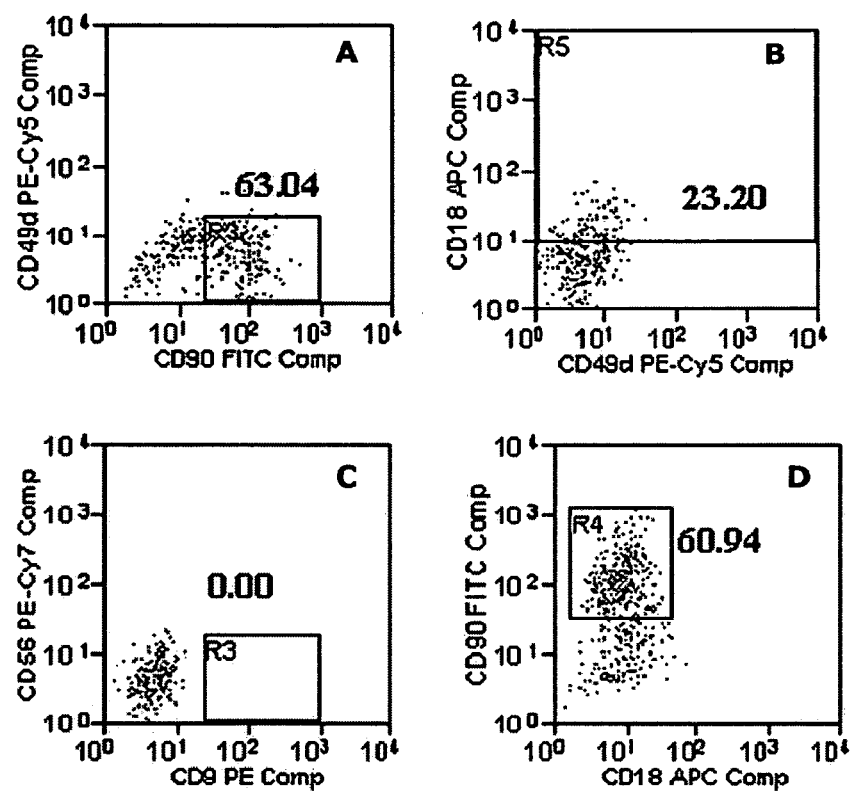
FIG. 10 depicts cell surface marker characterization of human adipose SP cells according to the teachings of the present invention.

Human adipose-derived stem cell SP cells were stained for the common stem cell antigens CD9, CD18, CD49d, CD56, and CD90. A high percentage of the cells expressed CD90, 61.1%±5%. Fewer ADSC-SP cells, 23.20%±7%, stained for CD18. The other markers, CD9, CD49d and CD56, were not present on the ADSC-SP cells (FIG. 10).

Example 5

Induction of Wound Healing with ADSC-SP Cells in Mice

Figure 11:
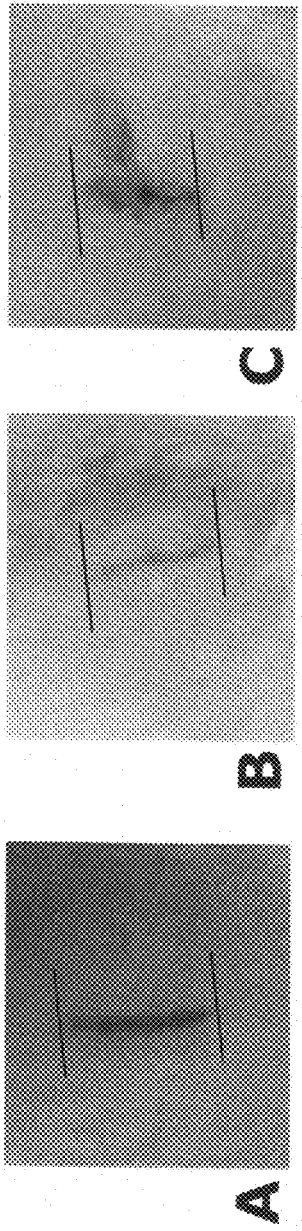
FIGS. 11A-F depict ADSC-SP-induced skin regeneration according to the teachings of the present invention one day (A-C) and 14 days (D-F) after injury in control mice (A and D) and in two mice implanted with human ADSC-SP cells (B, C, E, and F).
Figure 11:
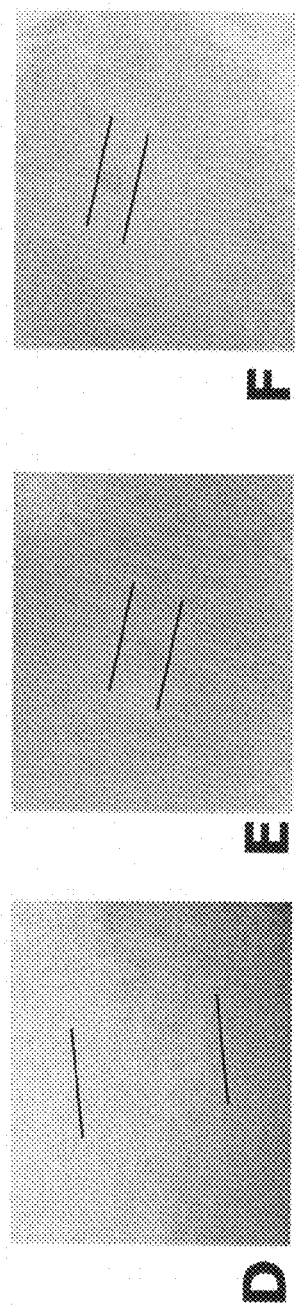

Approximately 10 cm incisions were made on the back of NOD/Scid mice (3 of animals per group) and the wound was left open. At approximately one minute after injury, 50,000 human ADSC-SP cells isolated as disclosed in Example 4 were injected at the site of the injury in one group of mice. A second group of mice received no cell transplantation (control group). At two weeks after injury, tissue sections of the injury site were taken to evaluate the extent of wound healing and tissue regeneration. FIG. 11 depicts gross evaluation of the injury site in control mice (A and D) and mice implanted with ADSC-SP cells (B, C, E and F) on day 1 (A-C) and day 14 (D-E). The scar seen in the control animal at 14 days (D) is less evident in the mice implanted with ADSC-SP cells (E and F).

Figure 12A:
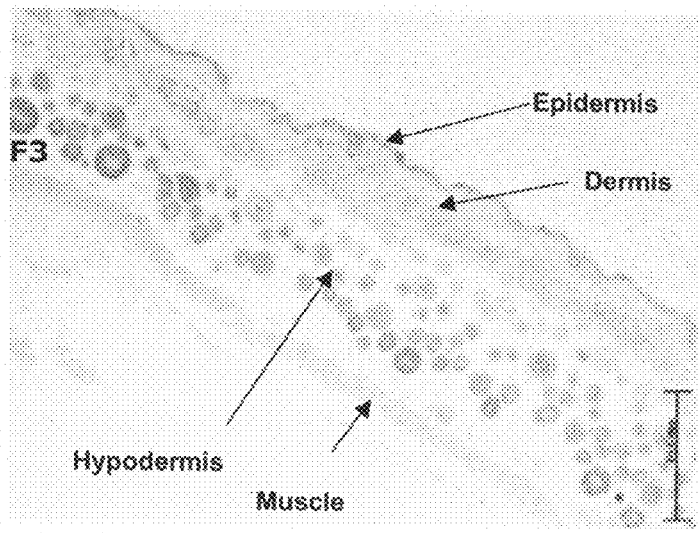
FIGS. 12A-C depict ADSC-SP-induced skin regeneration according to the teachings of the present invention two weeks after injury. Normal dermis (A), control mouse with no stem cells injected (B) and mouse implanted with human ADSC-SP cells into site of injury (C).
Figure 12B:
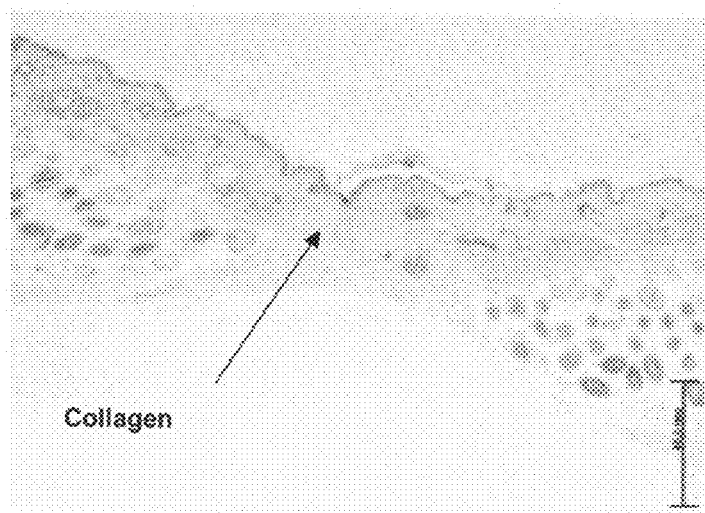
Figure 12C:
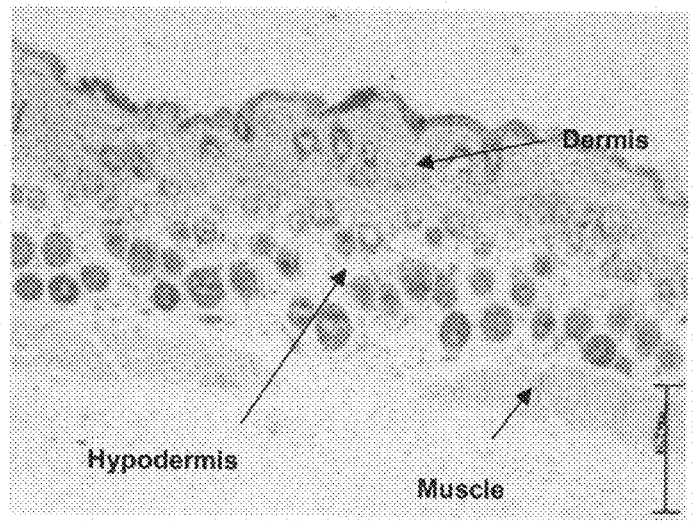

FIG. 12 depicts tissue sections from the injury site from both control mice and mice treated with ADSC-SP cells. FIG. 12A depicts normal dermis from a NOD/Scid mouse without an injury. Tissue sections from control mice 14 days after injury (FIG. 12B) demonstrated wound-induced disruption of skin architecture and formation of scar tissue. Tissue sections from mice implanted with ADSC-SP cells (FIG. 12C) demonstrated wound healing of restoration of normal skin architecture without evidence of scar tissue.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A therapeutic composition for promoting tissue regeneration in a mammal comprising isolated adipose-derived stem cell side population (ADSC-SP) cells, wherein said side population consists essentially of cells having the phenotype $Lin^-$, $Sca-1^+$, $CD90^+$, $CD34^{low}$, $CD13^{low}$, $CD117^-$ and $CD18^{low}$.

2. The therapeutic composition of claim 1 further comprising a pharmaceutically acceptable carrier.

3. The therapeutic composition of claim 1 wherein said mammal is a human.

4. An isolated mammalian adipose derived stem cell side population (ADSC-SP) wherein said isolated ADSC-SP cells comprise a subpopulation isolated from adipose-derived stem cell main population cells, and said isolated ADSC-SP cells consist essentially of cells having the phenotype $Lin^-$, $Sca-1^+$, $CD90^+$, $CD34^{low}$, $CD13^{low}$, $CD117^-$ and $CD18^{low}$.

5. The isolated mammalian ADSC-SP of claim 4 wherein said mammal is a human.

* * * * *